United States Patent
Poutous et al.

(10) Patent No.: US 9,857,295 B2
(45) Date of Patent: Jan. 2, 2018

(54) COMPARATIVE DISCRIMINATION SPECTRAL DETECTION SYSTEM AND METHOD FOR THE IDENTIFICATION OF CHEMICALS WITH OVERLAPPING SPECTRAL SIGNATURES

(71) Applicants: Menelaos K. Poutous, Charlotte, NC (US); Ishwar D. Aggarwal, Charlotte, NC (US); Kevin J. Major, Charlotte, NC (US); Jas S. Sanghera, Charlotte, NC (US); Ken Ewing, Charlotte, NC (US)

(72) Inventors: Menelaos K. Poutous, Charlotte, NC (US); Ishwar D. Aggarwal, Charlotte, NC (US); Kevin J. Major, Charlotte, NC (US); Jas S. Sanghera, Charlotte, NC (US); Ken Ewing, Charlotte, NC (US)

(73) Assignee: The University Of North Carolina At Charlotte, Charlotte, NC (US)

( * ) Notice: Subject to any disclaimer, the term of this patent is extended or adjusted under 35 U.S.C. 154(b) by 158 days.

(21) Appl. No.: 14/966,807

(22) Filed: Dec. 11, 2015

(65) Prior Publication Data
US 2017/0045442 A1  Feb. 16, 2017

Related U.S. Application Data

(60) Provisional application No. 62/203,077, filed on Aug. 10, 2015.

(51) Int. Cl.
*G01N 21/3504* (2014.01)
*G01N 21/35* (2014.01)

(52) U.S. Cl.
CPC ......... *G01N 21/3504* (2013.01); *G01N 21/35* (2013.01); *G01N 2201/1293* (2013.01)

(58) Field of Classification Search
CPC .................................................. G01N 21/3504
See application file for complete search history.

(56) References Cited

U.S. PATENT DOCUMENTS

| | | | |
|---|---|---|---|
| 3,364,351 A * | 1/1968 | Palmer ................ | G01N 21/314 250/338.5 |
| 6,266,428 B1 * | 7/2001 | Flanigan ............ | G01N 21/3504 250/336.1 |

(Continued)

*Primary Examiner* — David Porta
*Assistant Examiner* — Jeremy S Valentiner
(74) *Attorney, Agent, or Firm* — Clements Bernard Walker PLLC; Christopher L. Bernard (57) ABSTRACT

A comparative discrimination spectral detection (CDSD) system for the identification of chemicals with overlapping spectral signatures, including: a radiation source for delivering radiation to a sample; a radiation collector for collecting radiation from the sample; a plurality of beam splitters for splitting the radiation collected from the sample into a plurality of radiation beams; a plurality of low-resolution optical filters for filtering the plurality of radiation beams; a plurality of radiation detectors for detecting the plurality filtered radiation beams; and a processor for: receiving a set of reference spectra related to a set of target chemicals and generating a set of base vectors for the set of target chemicals from the set of reference spectra, wherein the set of base vectors define a geometrical shape in a configuration space; receiving a set of filtered test spectra from the plurality of radiation detectors and generating a set of test vectors in the configuration space from the set of filtered test spectra; assessing a geometrical relationship of the set of test vectors and the geometrical shape defined by the set of base vectors in the configuration space; and based on the assessed geometrical relationship, establishing a probability that a given test spectrum or spectra matches a given reference spectrum or spectra.

16 Claims, 9 Drawing Sheets

(56) References Cited

U.S. PATENT DOCUMENTS

| | | | |
|---|---|---|---|
| 2007/0279629 A1* | 12/2007 | Grun | G01J 3/28 356/318 |
| 2011/0290026 A1* | 12/2011 | Rice | G01N 21/1702 73/602 |
| 2012/0098924 A1* | 4/2012 | Busch | G01J 3/45 348/36 |

* cited by examiner

COMPARATIVE DISCRIMINATION SPECTRAL DETECTION SYSTEM AND METHOD FOR THE IDENTIFICATION OF CHEMICALS WITH OVERLAPPING SPECTRAL SIGNATURES

CROSS-REFERENCE TO RELATED APPLICATION

The present patent application/patent claims the benefit of priority of U.S. Provisional Patent Application No. 62/203, 077, filed on Aug. 10, 2015, and entitled "COMPARATIVE DISCRIMINATION SPECTRAL DETECTION (CDSD) ALGORITHM AND METHOD FOR THE IDENTIFICATION OF CHEMICALS WITH OVERLAPPING SPECTRAL SIGNATURES," the contents of which are incorporated in full by reference herein.

STATEMENT OF GOVERNMENT SPONSORED RESEARCH AND/OR DEVELOPMENT

The present invention was made with Government support by the Office of Naval Research, Award No. N00014-13-1-0208. Accordingly, the Government has certain rights in the present invention.

FIELD OF THE INVENTION

The present invention relates generally to an optical system and method for the identification of chemicals with overlapping spectral signatures. More specifically, the present invention relates to a comparative discrimination spectral detection (CDSD) system and method for the identification of chemicals with overlapping spectral signatures.

BACKGROUND OF THE INVENTION

Increasing the selectivity of chemical sensors, while at the same time reducing their complexity, size, and cost, are challenges to the sensing community. To this end, an area of exploration has been the development of filter-based chemical sensors and related methods.

Optical filter-based approaches to chemical sensing have the potential to develop simple, small, low-cost sensors with high selectivity. Such techniques can be designed in a manner that replicates the mechanism of human color vision, which utilizes three broadly overlapping filters to discriminate between over two million potential color hues. These approaches are used to identify multiple analytes in complex backgrounds in the near-infrared (near-IR), for example, such as glucose/urea and dimethyl methylphosphonate/diisopropyl methylphosphonate.

The present invention provides an approach that utilizes multiple, broadband, infrared (IR) filters to enable the discrimination of target chemicals in the presence of potential interferents that have IR spectral signatures in a limited waveband. This analysis technique, CDSD, utilizes a set of broad-IR transmission filters, to discriminate between a specific target chemical and multiple interferents with strongly overlapping IR spectra.

The CDSD approach has some similarities to previously existing methods, but is different in many respects. For example, CDSD requires that filtered data be used, but both expands the dimensionality of the configuration-space, and employs comparative relationships between the filter responses of the various chemicals in a given set. Other approaches use a filter-defined configuration vector space within which an attempt is made to find projections that separate chemical signatures from their background. These approaches are configuration-space reduction methods, whereas CDSD is a higher-dimensionality space-expansion method. Other filter-based detection approaches include Programmable Correlation Radiometry, a spectral comparative-radiometry technique, and Multivariate Optical Elements, which use multilayer interference filters, whose transmission spectra represent the features of a spectral regression vector within a given spectral region. Programmable Correlation Radiometry uses correlation spectroscopy and synthetic spectra as a basis for the remote detection of chemical species. Contrary to sensing using techniques such as Programmable Correlation Radiometry or Multivariate Optical Elements, CDSD does not attempt to resolve spectral differences based on optical filter selectivity characteristics. On the contrary, CDSD uses low-resolution, large-bandwidth, overlapping spectral filters to construct the chemical representative vectors in order to explore the relationships between the vectors, as well as their commonly constructed surfaces and volumes. Thus, rather than using complex optical elements, the biomimetic CDSD approach relies on individual chemical responses to simple shaped band-pass optical filters. Therefore, the CDSD method provides a new data processing and detection approach for photometric systems.

The numerical method is not an iterative search, such as Principal Component Analysis (PCA), or a type of linear discriminant analysis (LDA). It actually increases the dimensions in configuration-space, where the computations are performed, instead of decreasing them, as both PCA and LDA do.

BRIEF SUMMARY OF THE INVENTION

Thus, the present disclosure describes a specific computational algorithmic routine and method to identify chemicals within non-interacting chemical mixtures, based on a high-dimensionality configuration-space comparative method. The computational algorithmic routine's function is to separately identify chemical spectral signatures that can have large overlap (common spectrum structure) with other undesirable materials. The computer-implemented methods and processes provide a major computational advantage over analytical methods (i.e., PCA and LDA), and can discriminate between target chemicals and very closely matched interferants. They allow for binary outcome detection (i.e., Yes/No), or relative density detection, proportional to the amount of chemical present in the mixture under test.

In one exemplary embodiment, the present invention provides a comparative discrimination spectral detection (CDSD) system for the identification of chemicals with overlapping spectral signatures, comprising: a radiation source operable for delivering radiation to a sample; a radiation collector operable for collecting radiation from the sample; a plurality of beam splitters operable for splitting the radiation collected from the sample into a plurality of radiation beams; a plurality of low-resolution optical filters operable for filtering the plurality of radiation beams; a plurality of radiation detectors operable for detecting the plurality filtered radiation beams; and a processor operable for: receiving a set of reference spectra related to a set of target chemicals and generating a set of base vectors for the set of target chemicals from the set of reference spectra, wherein the set of base vectors define a geometrical shape in a configuration space; receiving a set of filtered test spectra from the plurality of radiation detectors and generating a set of test vectors in the configuration space from the set of filtered test spectra; assessing a geometrical relationship of the set of test vectors and the geometrical shape defined by the set of base vectors in the configuration space; and based on the assessed geometrical relationship of the set of test vectors and the geometrical shape defined by the set of base vectors in the configuration space, establishing a probability that a given test spectrum or spectra matches a given reference spectrum or spectra. The radiation source comprises an infrared (IR) illuminator for the waveband of interest, such as a limited thermal radiation source, a glowbar or photo-emmissive diode, or an infrared waveband (IRWB) laser or laser diode, for example, that emits radiation in the near-infrared (NIR), the mid-wave infrared (MWIR), or the long-wave infrared (LWIR), including the required optics to project the illuminating beam the distance required for the desired application. The radiation collector comprises an IR-compatible optical system of lenses and windows (which may be made of materials such as sapphire ($Al_2O_3$), zinc sulfide (ZnS), zinc selenide (ZnSe), silicon (Si), and/or germanium (Ge)) used in a non-imaging configuration to concentrate the light from the field into the internal optical path of the instrument. The plurality of beam splitters each comprise optical plates with specific optical reflections (e.g., 5-15%) and transmissions (e.g., 85-95%), made from calcium fluoride ($CaF_2$), silicon (Si), zinc selenide (ZnSe), and/or fused silica ($SiO_2$). The plurality of low-resolution optical filters each comprise glass filters, made of silicon (Si), zinc selenide (ZnSe), and/or quartz, with wavelength pass-bands peaked at the wavelength of interest in the MWIR (i.e., 3-5 µm) or the LWIR (i.e., 8-12 µm) and with a bandwidth matched to the detectors and software requirements for the specific chemicals to be detected—these bandwidths typically on the order of 20-100 nm. The plurality of radiation detectors each comprise thermal or photon detectors, such as bolometers, pyroelectrics, thermopiles, or Golay cells, or photoconductors, photovoltaics, or photodiodes. The set of base vectors define a polygon having a volume in the configuration space. If the given test spectrum or spectra matches the given reference spectrum or spectra, then a given test vector will fall at least partially within the volume of the polygon in the configuration space and have predetermined relationships with the sides and surface normals of the polygon. If the given test spectrum or spectra does not match the given reference spectrum or spectra, then a given test vector will fall at least partially outside of the volume of the polygon in the configuration space and not have predetermined relationships with the sides and surface normals of the polygon.

In another exemplary embodiment, the present invention provides a comparative discrimination spectral detection (CDSD) method for the identification of chemicals with overlapping spectral signatures, comprising: delivering radiation to a sample using a radiation source; collecting radiation from the sample using a radiation collector; splitting the radiation collected from the sample into a plurality of radiation beams using a plurality of beam splitters; filtering the plurality of radiation beams using a plurality of low-resolution optical filters; detecting the plurality filtered radiation beams using a plurality of radiation detectors; and providing a processor operable for: receiving a set of reference spectra related to a set of target chemicals and generating a set of base vectors for the set of target chemicals from the set of reference spectra, wherein the set of base vectors define a geometrical shape in a configuration space; receiving a set of filtered test spectra from the plurality of radiation detectors and generating a set of test vectors in the configuration space from the set of filtered test spectra; assessing a geometrical relationship of the set of test vectors and the geometrical shape defined by the set of base vectors in the configuration space; and based on the assessed geometrical relationship of the set of test vectors and the geometrical shape defined by the set of base vectors in the configuration space, establishing a probability that a given test spectrum or spectra matches a given reference spectrum or spectra. The radiation source comprises an IR illuminator for the waveband of interest, such as a limited thermal radiation source, a glowbar or photo-emmissive diode, or an IRWB laser or laser diode, for example, that emits radiation in the NIR, the MWIR, or LWIR, including the required optics to project the illuminating beam the distance required for the desired application. The radiation collector comprises an IR-compatible optical system of lenses and windows (which may be made of materials such as sapphire ($Al_2O_3$), zinc sulfide (ZnS), zinc selenide (ZnSe), silicon (Si), and/or germanium (Ge)) used in a non-imaging configuration to concentrate the light from the field into the internal optical path of the instrument. The plurality of beam splitters each comprise optical plates with specific optical reflections (e.g., 5-15%) and transmissions (e.g., 85-95%), made from calcium fluoride ($CaF_2$), silicon (Si), zinc selenide (ZnSe), and/or fused silica ($SiO_2$). The plurality of low-resolution optical filters each comprise glass filters, made of silicon (Si), zinc selenide (ZnSe), and/or quartz, with wavelength pass-bands peaked at the wavelength of interest in the MWIR (i.e., 3-5 µm) or the LWIR (i.e., 8-12 µm) and with a bandwidth matched to the detectors and software requirements for the specific chemicals to be detected—these bandwidths typically on the order of 20-100 nm. The plurality of radiation detectors each comprise thermal or photon detectors, such as bolometers, pyroelectrics, thermopiles, or Golay cells, or photoconductors, photovoltaics, or photodiodes. The set of base vectors define a polygon having a volume in the configuration space. If the given test spectrum or spectra matches the given reference spectrum or spectra, then a given test vector will fall at least partially within the volume of the polygon in the configuration space and have predetermined relationships with the sides and surface normals of the polygon. If the given test spectrum or spectra does not match the given reference spectrum or spectra, then a given test vector will fall at least partially outside of the volume of the polygon in the configuration space and not have predetermined relationships with the sides and surface normals of the polygon.

BRIEF DESCRIPTION OF THE DRAWINGS

The present invention is illustrated and described herein with reference to the various drawings, in which like reference numbers are used to denote like system components/method steps, as appropriate, and in which:

FIG. 7 is a plurality of plots illustrating matching indicator signals (top graphs) and weighted discrimination results $\alpha$, $\beta$, and $\gamma$ (lower graphs) for acetone vapors—$\alpha$, hexanes vapors—$\beta$, and fuel oil vapors—$\gamma$ for two tests: (a) test with only acetone vapors; and (b) test with only fuel oil vapors—the discrimination operations are weighted to the maximum value of the $\alpha+\beta+\gamma$ sum in each test and the matching indicator signal registers 1 (left of the vertical dashed line on (a) and right of the dashed line on (b)) if the test has matched vectors from the chemical set, or >>1 (right of the dashed line on (a) and left of the dashed line on (b)) if there are no matches in the test (note that the matching signal fails (>>1) if there is nothing to detect);

FIG. 8 is a plurality of plots illustrating matching indicator signals (top graphs) and weighted discrimination results $\alpha$, $\beta$, and $\gamma$ (lower graphs) for acetone vapors—$\alpha$, hexanes vapors—$\beta$, and fuel oil vapors—$\gamma$ for two tests with mixtures: (a) test starting with equal volumes of acetone and fuel oil; and (b) test starting with equal volumes of hexanes and fuel oil—the discrimination operations are weighted to the maximum value of the $\alpha+\beta+\gamma$ sum in each test and the matching indicator signal registers 1 if the test has matched vectors from the chemical set, or >>1 if there are no matches in the test (note that the matching signal shows a result (=1) for the duration of both tests, indicating the presence of vapors throughout the experimental time from the selected set.

DETAILED DESCRIPTION OF THE INVENTION

In general, CDSD is a spectrum identification technique based on similarities between an established set of spectral signatures and an unknown spectrum to be tested. It is used to discriminate between very similar spectral signatures of non-reacting chemicals within a limited spectral band, and allows for the estimation of the chemical components in a mixture or the presence of unmixed chemicals in a spectrally "cluttered" background environment.

Figure 1:
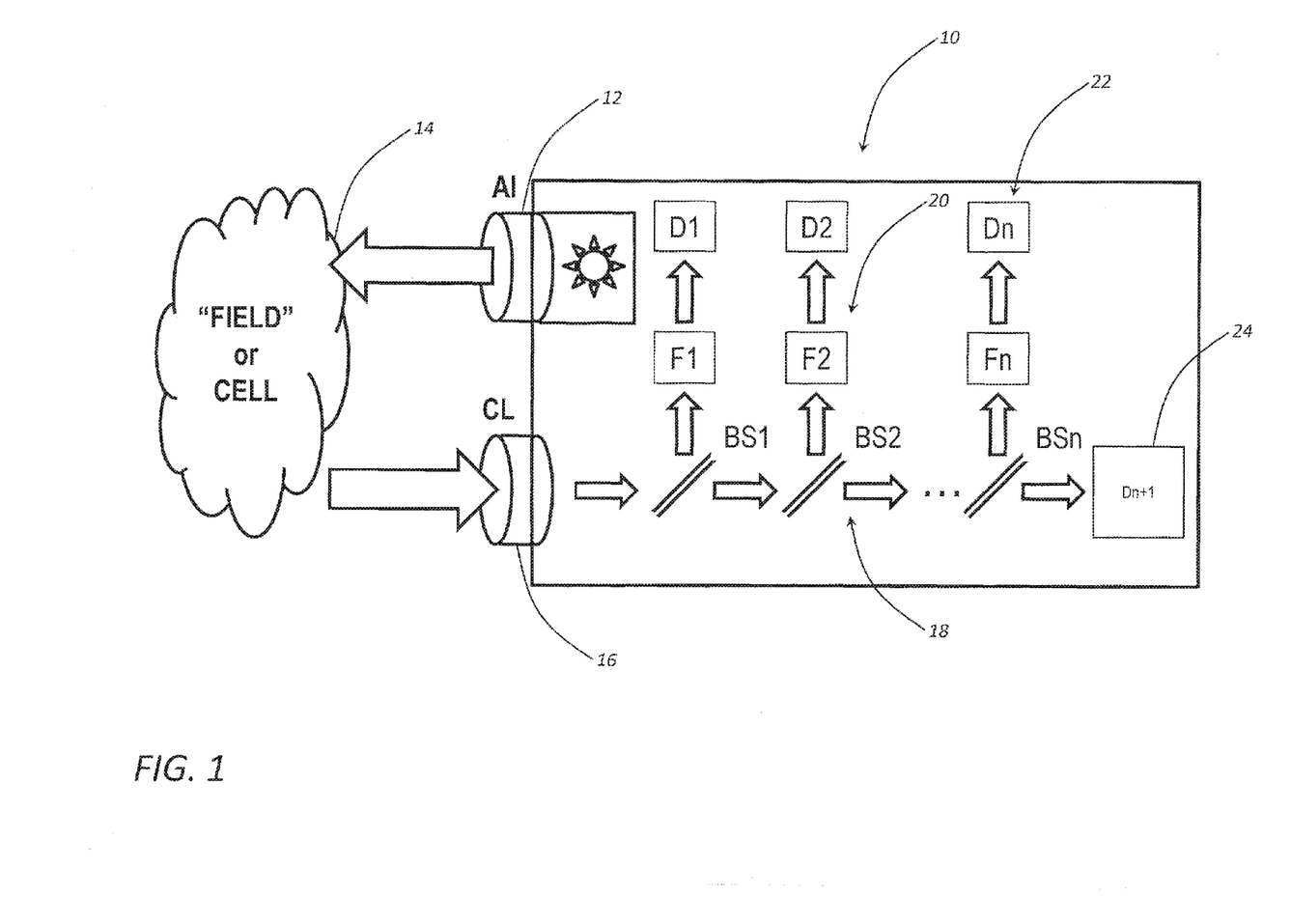
FIG. 1 is a schematic diagram illustrating one exemplary embodiment of the CDSD system of the present invention.

Referring now specifically to FIG. 1, in one exemplary embodiment, the CDSD system 10 of the present invention includes an active illuminator 12, such as a laser or other light source, including beam projection optics that are capable of illuminating a "field" or cell 14. The CDSD system 10 also includes light collection optics 16 that are capable of collecting light from the "field" or cell 14. These light collection optics 16 may include, for example, optical systems of lenses and windows (made from materials like sapphire ($Al_2O_3$), zinc sulfide (ZnS), zinc selenide (ZnSe), silicon (Si), and/or germanium (Ge)) used in non-imaging configurations. The collected light is run through a plurality of optical broadband beam splitters 18, such as a plurality of optical plates, with specific optical reflections (e.g., 5-15%) and transmissions (e.g., 85-95%), made from calcium fluoride ($CaF_2$), silicon (Si), zinc selenide (ZnSe), and/or fused silica ($SiO_2$), that feed a plurality of optical low-resolution filters 20 (n-optical transmission filters of finite but limited band), such as a plurality of glass filters, made of silicon (Si), zinc selenide (ZnSe), and/or quartz, and a plurality of associated optical detection elements 22, such as a plurality of thermal detectors (such as bolometers, pyroelectrics, thermopiles, or Golay cells) or photon detectors (such as photoconductors, photovoltaics, or photodiodes). Finally, an unfiltered reference detector 24 is provided.

Figure 2:
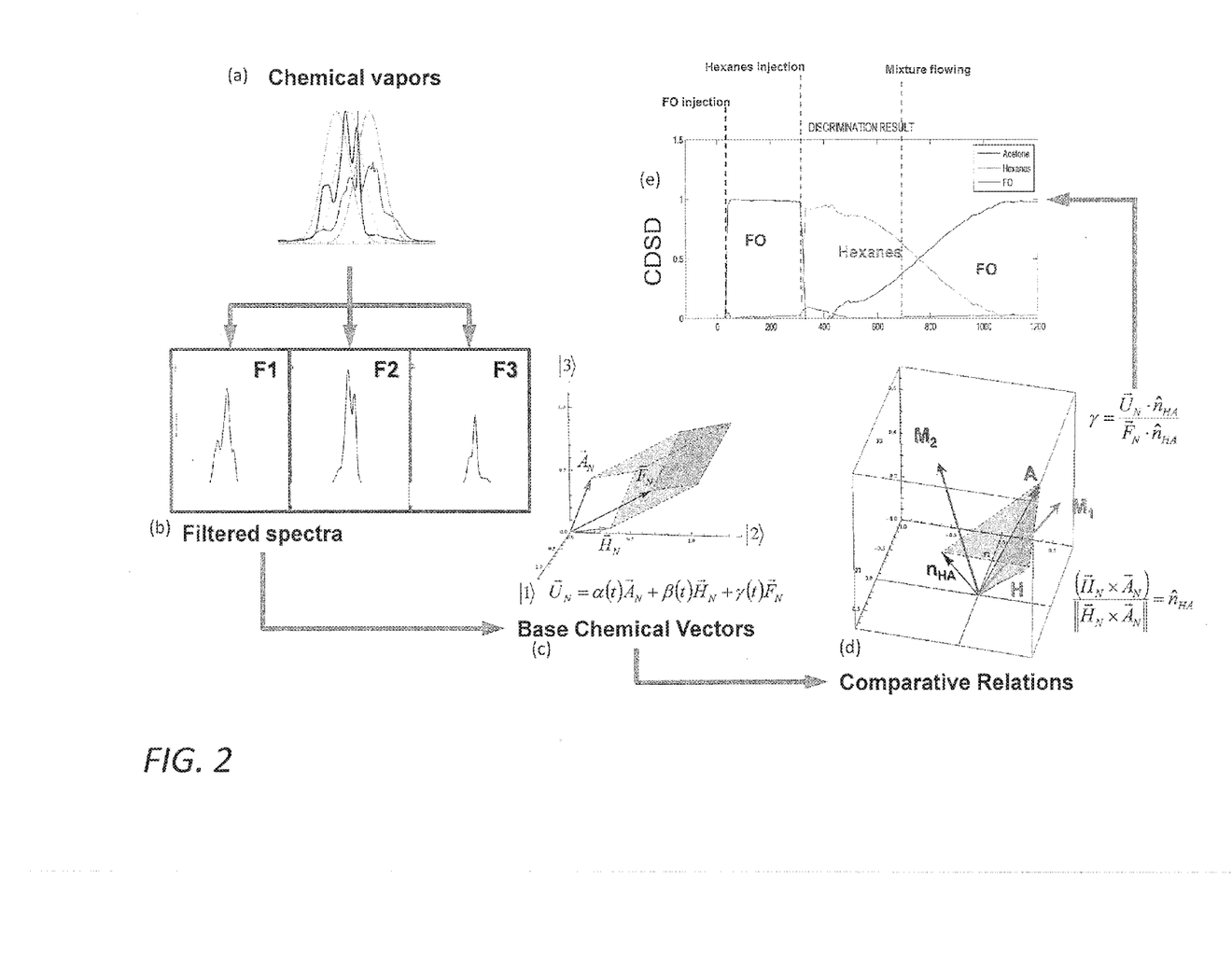
FIG. 2 is a schematic diagram illustrating one exemplary embodiment of the CDSD method of the present invention.
Figure 3:
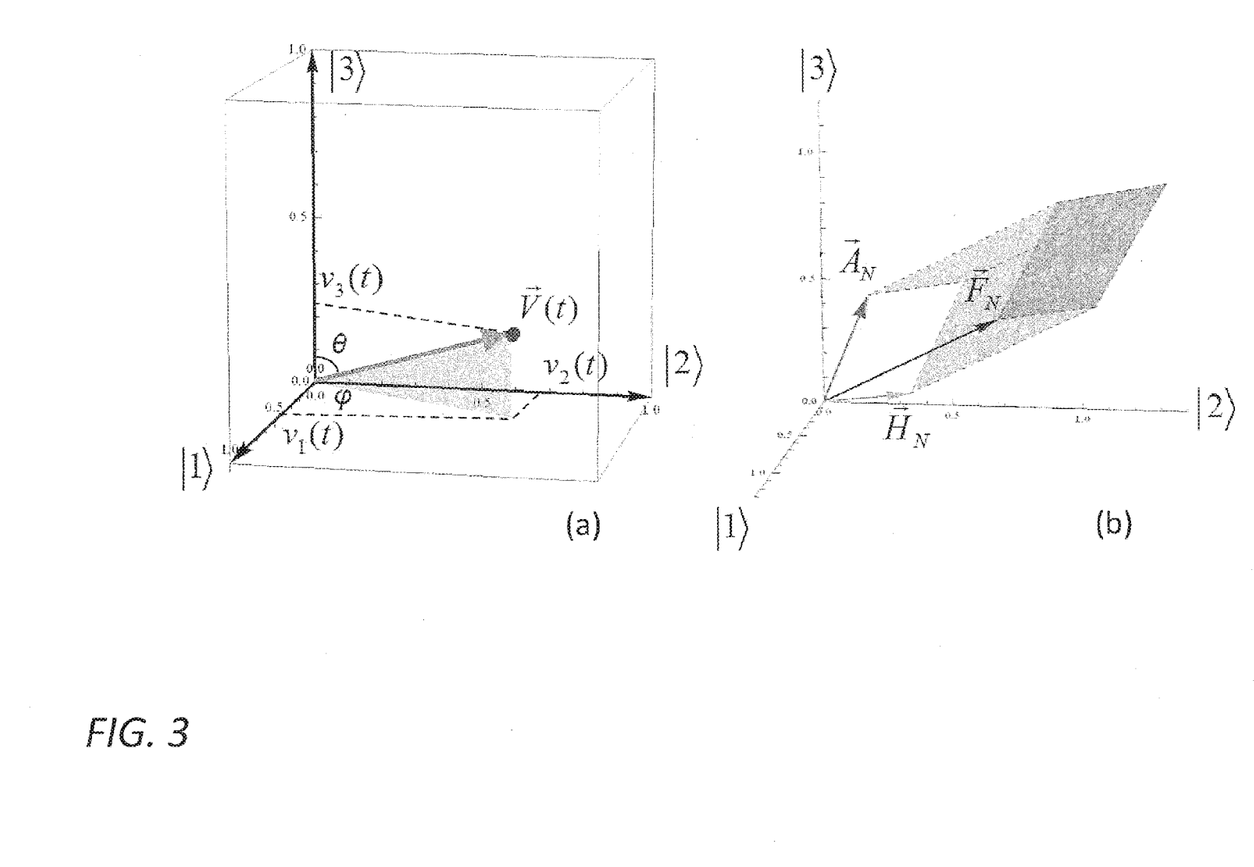
FIG. 3 is a pair of plots illustrating: (a) normalized chemical vector (V(t)) representing a particular chemical at an instance in time, t—the components of the vector are equal to the ratios of the detected absorption through each optical filter implemented (here there are here); and (b) configuration space volume defined by three normalized chemical vectors ($A_N$, $F_N$, and $H_N$)—the volume has a non-zero value only if the vectors are all distinct from one another.
Figure 4:
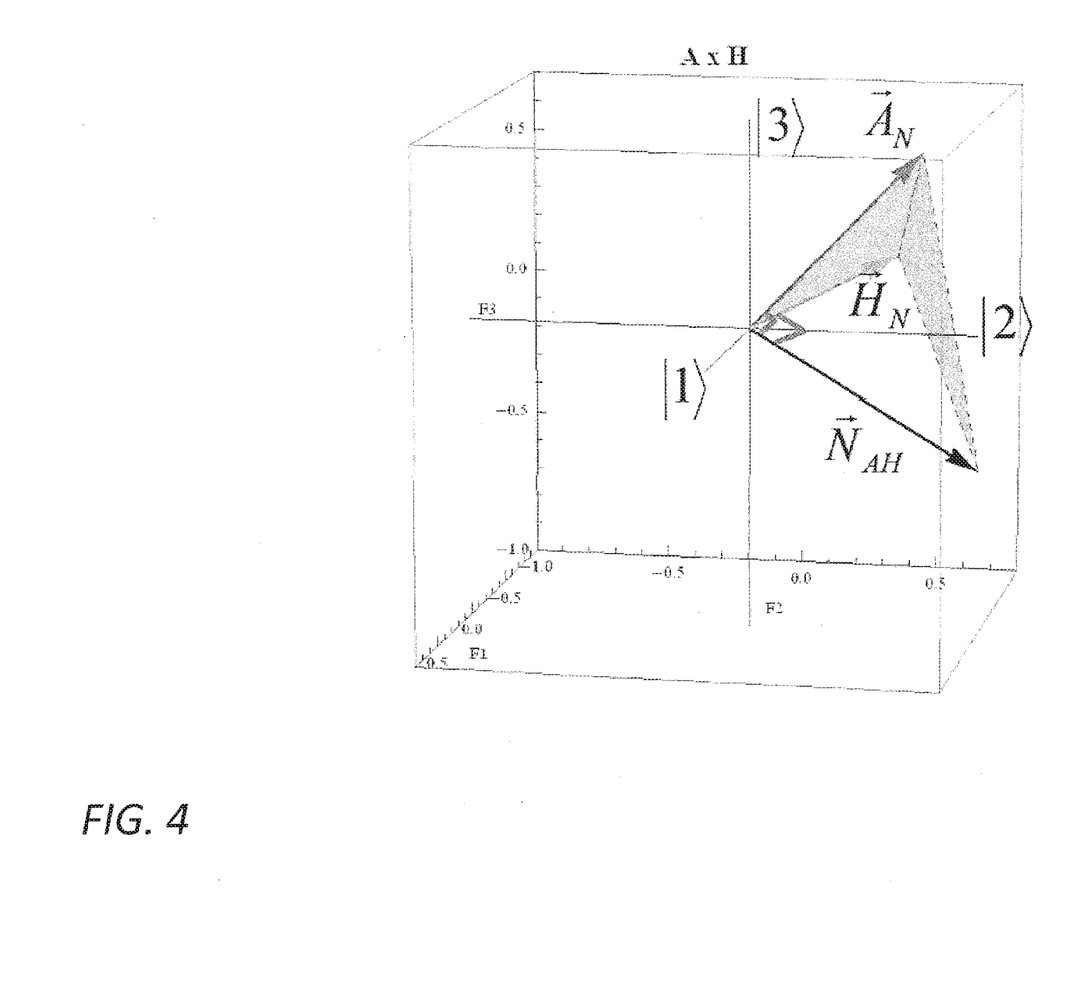
FIG. 4 is a plot illustrating the result of the vector product geometrical operation $(A_N \times H_N) = N_{AH}$—the vector $N_{AH}$ is perpendicular to both $A_N$ and $H_N$, and thus any vector that is their linear combination is also perpendicular to $N_{AH}$.
Figure 5:
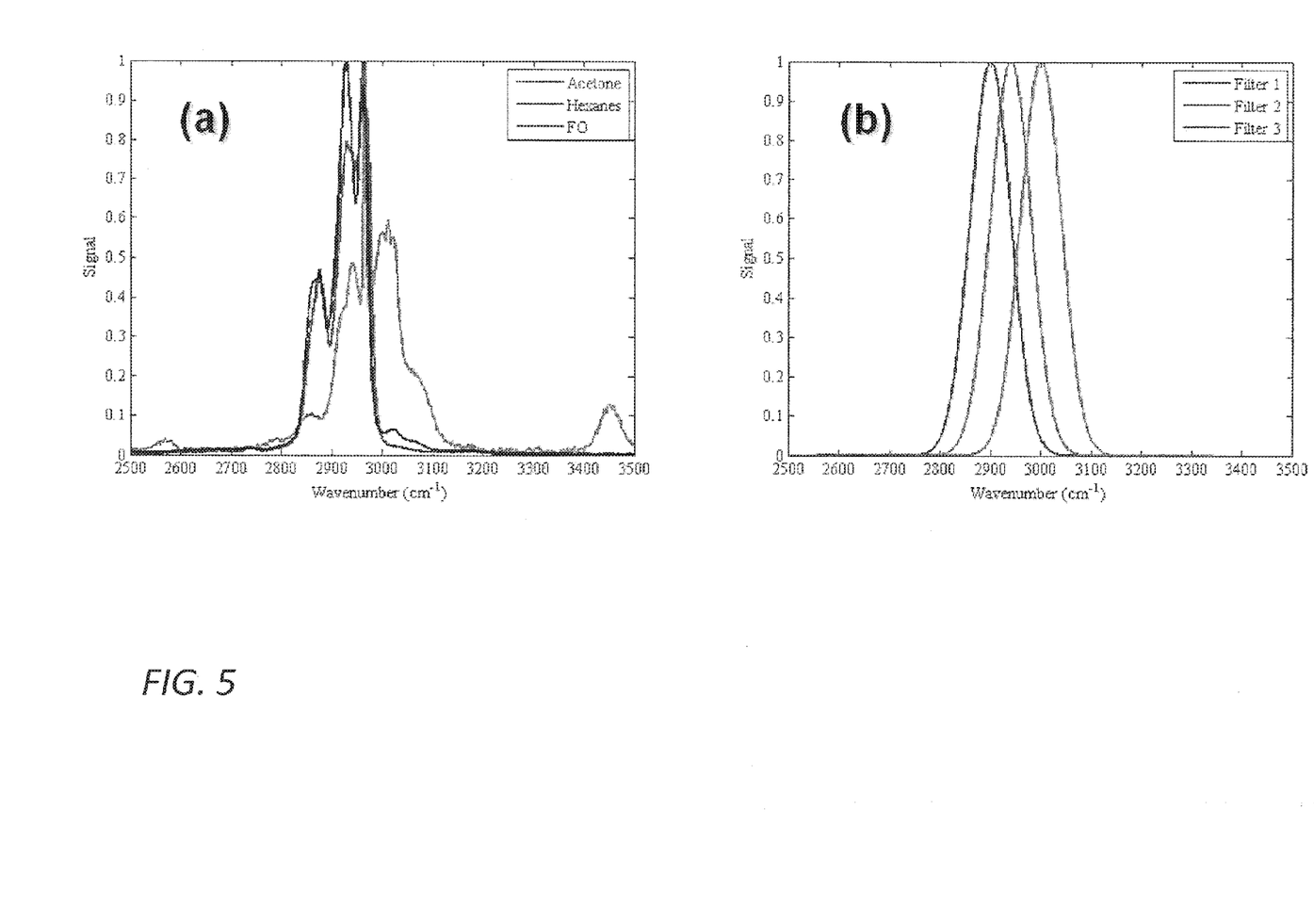
FIG. 5 is a pair of plots illustrating: (a) absorption spectra for three sample chemicals (acetone, hexanes, and fuel oil) with high spectral overlap; and (b) sample optical bandpass or numerical processing filters used to generate the components of the chemical vectors for each chemical of interest.

The CDSD technique requires first having a collection of well characterized spectra from the desired "target" chemical or chemicals to be identified (see FIG. 2). Using the set of optical low-resolution filters 20, the total detectable spectral power within the filter bandwidth is collected by the set of n detectors 22, resulting in a list of values representing the total integrated spectral response of the target signatures under the optical filter limits. This list of values is then used to construct n-dimensional vectors of unit magnitude within the n-spectral filter orthonormal configuration space, which has no statistical or physical interpretation (see FIG. 3). It is equivalent only to the relative response of the target spectrum to the optical filter band-pass. For a group of m-chemical targets, there are m normalized vectors of n-dimensions, each uniquely representing a target chemical. These are called "base" or "target" vectors. The m base vectors define a polygon in the n-dimension configuration space. Any test spectrum signature that is collected through the existing optical low-resolution filters 20, can be expressed as a normalized-magnitude test vector in the same configuration space. If the test vector is a linear combination of any, or all, of the base vectors, it has definite geometrical relations with the base vector polygon's sides and surface normals. More specifically, if the test vector is only a linear combination of the existing base vectors, then it lies within the polygon volume. Further, it has projections to all surface normals of the polygon's sides (see FIG. 4). If the test vector lies outside the polygon volume, it may be expressed as a linear combination of components internal and external to the polygon. However, it will not have projections to all side surface normals, as it is not possible to be orthogonal to all of them. These orthogonality criteria serve as the discrimination rules for the test vectors (i.e., chemicals). The test vectors are compared to the polygon side surface normal and, based on the comparison results, a "truth" table is assembled. The truth table has three possible value entries: 0, 1 and >>1 (see FIG. 5). In the case of a 0 outcome, the test vector does not have a component within the polygon side defined by the particular base vectors. In the case of a 1 outcome, the possibility exists that the test vector is made of a linear combination of the two base vectors acting as the edges of the polygon side. For an outcome >>1, there is no possibility that the test vector is made by any component of the base set. The results of the truth table are further compared within the possible outcomes, to discriminate for cases of contradiction in result. At the end of the comparative step between the table outcomes, a likelihood of detection is the output. The operations reduce the possibilities to a binary outcome, of "yes" or "no" concerning the presence of any of the m target chemicals in the test material.

Figure 6A:
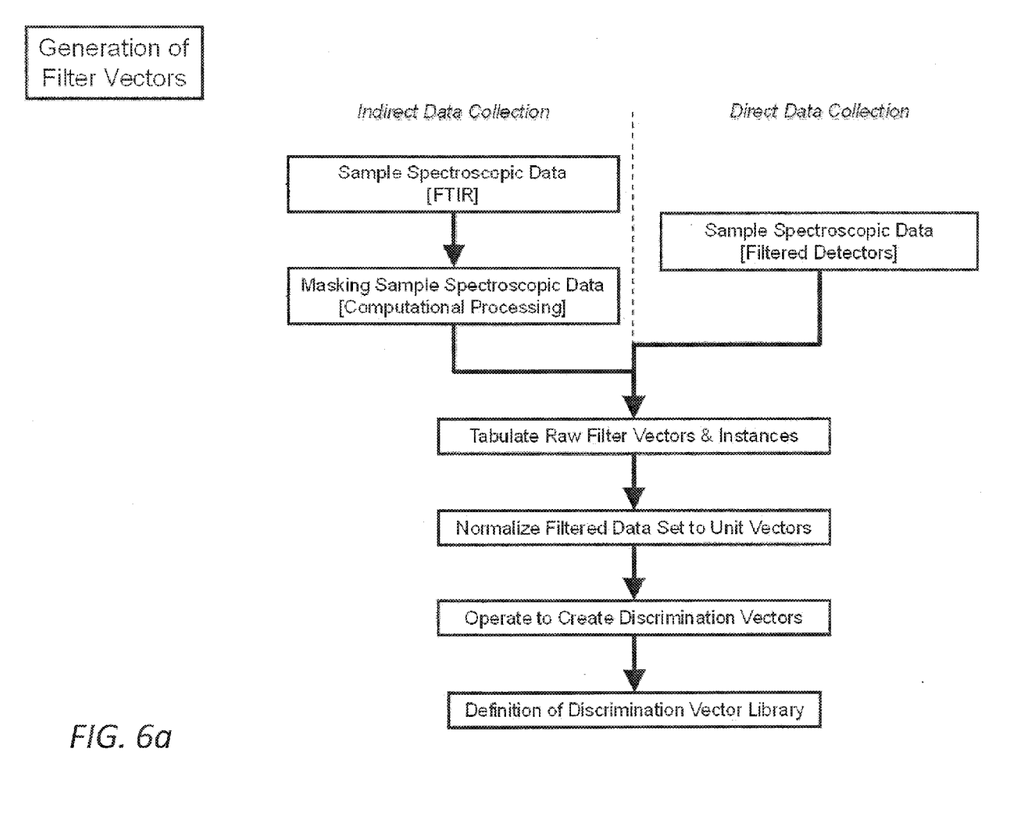
FIG. 6a is a flowchart illustrating one exemplary embodiment of a computer implemented algorithm for executing the CDSD method of the present invention.
Figure 6B:
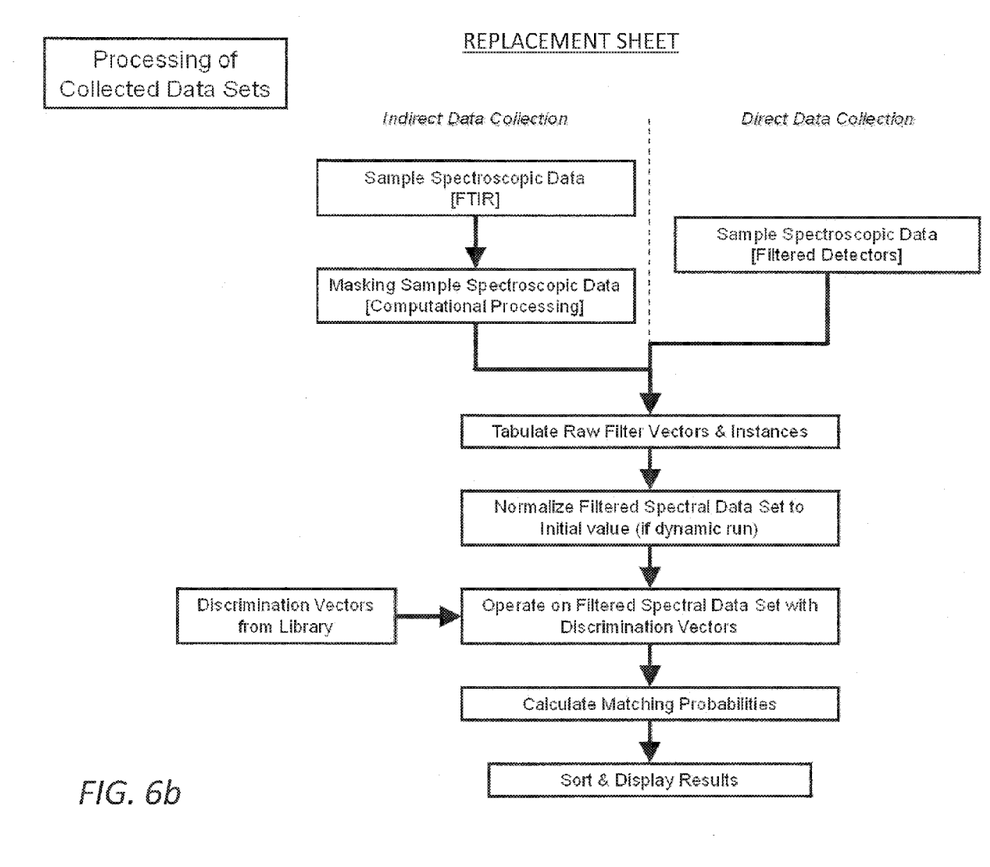
FIG. 6b is another flowchart illustrating another exemplary embodiment of a computer implemented algorithm for executing the CDSD method of the present invention.

The CDSD method is based on the initial collection of the spectral absorption signal from a set of "pure" chemical vapors of interest that have similar absorption bands and therefore strongly overlapping spectra. It then uses optical functions as broad-wavelength extent band-pass filters and computes the overlap of the vapor spectrum with the filter set (see FIG. 6). The filters are not only broadband, but also can be overlapping with each other as well. The resulting numbers form a set of unit vectors in an abstract configuration space, each representing a pure vapor, which is then used to define a volume through the triple vector product operation: A×B×C. The method takes advantage of the fact that any test vapor unit vector (of a mixture or a pure chemical outside the original set), will either be inside this volume or outside of it. If the test vector is inside the volume, and can be expressed by a linear combination of the three chosen pure unit vectors, it will have specific vector product relations with the defined volume. If the test vector is not inside the volume, it will have different product relations. The method uses the vector and scalar product operations of the test vector with the pure vapor vectors in order to identify the test vector as a part of the volume or external to it. Below are results from experimental measurements of pure and mixed vapors, as well as tests with vapors outside the chosen set.

One embodiment of the computer program flow is shown schematically in FIG. 6. The computer algorithm calculations are based on the following analysis. Considering the IR light absorption of as-received chemical vapors, or a mixture of non-reacting vapors from different substances, the spectral signal can be "filtered" in wave-vector space using a windowing function $F_1(k,k_1,\delta k_1)$, such that:

$$v_f(t) = \int_{\Delta k} [F_{1f}(k, k_f, \delta k_f)S(k, \Delta k, t)]dk \geq 0 \quad (1)$$

where $S(k,\Delta k,t)$ is the absorption signal in the 2500-3500 cm$^{-1}$ spectral range, $\Delta k$, at time t, and $v_1(t)$ is the resulting spectral-filter overlap integral value; with index 1 identifying the filtering window from a predetermined set of such filters. The filter window function $F_1(k,k_1,\delta k_1)$ can be of arbitrary complexity, as long as it is finite and positive over all wave-vectors, and $\delta k_1 < \Delta k$, i.e., the spectral extent of filter 1 ($\delta k_1$) is smaller than the collected spectral signal extent. The filter window function location within $\Delta k$ is identified by the wave-number $k_1$, which is the midpoint of its extent $\delta k_1$. As mentioned above, the original spectral signal sets collected could be changing in time, as gases move through the detection apparatus, or as evaporation changes the finite mixture contents under test. The maximum value of the filtering window function is normalized to unity, with the result $v_1(t)$ as the area under the filtered spectral signal, bounded by the shape of the filter $F_1(k,k_1,\delta k_1)$. The shape of each filtering window function is chosen so that no two filters are identical, even though they could overlap with each other, and also to allow for different broad spectral extents, $\delta k_1$. The CDSD method utilizes an abstract 1-dimensional orthonormal configuration space, where the basis unit vectors are the filter windowed responses to a uniform background spectrum of unit value over the range $\Delta k$, i.e., $S(k,\Delta k,t)=1$. The area under each filtering window operation generates a set of non-unique values, which are then used to create a configuration space vector for each vapor (or vapor mixture) analyzed. In the present case, a set of three windowing filter functions ($F_1$, $F_2$, $F_3$) are constructed, so that the result of the spectral "filtering" using Eq. 1, at a certain absorption spectrum from an instance t, is expressed as the vector:

$$v_m(t) = v_{1m}(t)|1\rangle + v_{2m}(t)|2\rangle + v_{3m}(t)|3\rangle \quad (2)$$

where $v_m(t)$ is the configuration-space v representing the three windowed responses $v_{1m}(t)$ in the basis ($F_1$, $F_2$, $F_3$) for vapor m. This representation is abstract, since the configuration space has no physical meaning other than the response of the signal windowed by the chosen filters. It can be considered as a specific "cataloging fingerprint" of the vapors tested, representing a set of values with no limitations to the number of filters one can use to construct it. The imposed condition is that the basis unit vectors are purposely constructed with directions that obey vector orthonormality conditions.

The CDSD method requires at least three overlapping filter windows, to investigate three chemicals, such as: acetone, hexanes, and fuel oil. Further, each vector represents a chemical vapor from the set: acetone, hexanes and fuel oil, and should be uniquely identifiable. Since the component values of the vector can only be positive, due to the choice of only positive windowing functions, $v_m(t)$ exist only in the space of positive values of $v_{1m}(t)$. Such a vector is depicted in FIG. 3a.

Temporal changes of the spectral signal $S_m(k,\Delta k,t)$ of a chemical vapor m can be separable from the spectrum, indicating that the spectrum is a scaled function of time T(t), such that:

$$S_m(k, \Delta k, t) = \quad (3)$$

$$S_m(k, \Delta k)T(t) \Rightarrow v_{bn}(t) = T(t)\int_{\Delta k} [F_f(k, k_f, \delta k_f)S_m(k, \Delta k)]dk = T(t)v_{bn}$$

Since the filter windowing function is chosen to be time independent, this implies that the resulting filtered spectral vector components, $v_{1m}$, are also time independent. In the case of a flowing system detecting a specific vapor, T(t) could be an exponential decaying function, or an increasing function, completely dependent on the evaporation rate of the chemical and experimental conditions. In the case of a closed stationary gas system, the value of the scaling function can be set to unity, as it is constant.

Eq. 3 implies that, for data from vapors of chemical m, the time evolution of the representative $v_m(t)$ can be separated from the components of the vector describing the vapor. Therefore, time scaling affects only the magnitude of the vector, and not its direction in the configuration space. If one normalizes the vectors with respect to the maximum magnitude within the set of spectra collected, time evolution is represented as a contraction or expansion of $v_m(t)$, with a maximum value of 1. This non-interacting vapor vector normalization allows the removal of scaling differences between different sets of collected data, taken under different conditions, involving the same chemical m.

When one uses the vector operation of the scalar triple-product to define a set of selection rules, relating the uniqueness of the as-received chemical vapor vectors for different sets of experiments, the vapors from the three exemplary chemicals tested are stable mixtures of non-interacting components, and are non-interacting between them as well. The set of vapor vectors selected should be unique to identify each as-received chemical vapor, from mixtures of these vapors with each other. For a set of three non-identical normalized vapor vectors $a_N$, $f_N$, and $h_N$, corresponding respectively to acetone, fuel oil, and hexanes, the scalar triple-product is:

$$a_N \cdot (f_N \times h_N) = h_N \cdot (a_N \times f_N) = f_N \cdot (h_N \times a_N) \neq 0 \quad (4)$$

Eq. 4 is geometrically depicted as the volume defined by the three vapor vectors in the configuration space of filters ($F_1$, $F_2$, $F_3$) in FIG. 3b. The volume is bound by the three vectors and Eq. 4 is a sufficient condition to imply that the vectors are not co-planar. Therefore, one can use the set of predetermined filter windows from Eq. 1 to generate the volume by Eq. 4 and test measured spectral vectors to determine if they are included inside this volume, or reside outside of it. If a test vapor vector is used as part of the projection operation (dot product) into the vector cross products of Eq. 4, the result discriminates with respect to the constituents of the cross product. The terms inside the parentheses of Eq. 4 define a geometric surface in configuration space. If the test vector is not contained within this surface, the triple product results in a non-zero value less than unity, indicating that the vector is inside the abstract volume. If the test vector is outside the volume, and by consequence not on any of the surfaces bounding the volume, the projection will be greater than unity or negative. Computing the properties of the vapor representing normalized vectors $a_N$, $f_N$, and $h_N$, one finds the orthonormal unit-vector representing each of the surfaces as $n_{ML}$ (see FIG. 4):

$$\frac{(h_N \times a_N)}{\|h_N \times a_N\|} = n_{HA}; \quad \frac{(a_N \times f_N)}{\|a_N \times f_N\|} = n_{AF}; \quad \frac{(f_N \times h_N)}{\|f_N \times h_N\|} = n_{FH} \quad (5)$$

The vector projections of $a_N$, $f_N$, and $h_N$ on each one of the above normal unit vectors result in the discrimination table:

$a_N \cdot n_{HA} = 0 \quad a_N \cdot n_{AF} = 0 \quad a_N \cdot n_{FH} \neq 0$ $h_N \cdot n_{HA} = 0 \quad h_N \cdot n_{AF} \neq 0 \quad h_N \cdot n_{FH} = 0$ $f_N \cdot n_{HA} \neq 0 \quad f_N \cdot n_{AF} = 0 \quad f_N \cdot n_{FH} = 0 \quad (6)$ The table indicates that the unit normal to each surface, defined by its respective vectors, is perpendicular to both of these vectors and not to the third. Eqs. 6 can be viewed as a logical table, where normal vectors discriminate with respect to their generators, but not to another non-identical vector. If a test vapor vector $u_N$ contains a linear combination of mixed vapor vectors $a_N$, $f_N$, and $h_N$, such that:

$$u_N = \alpha(t)a_N + \beta(t)h_N + \gamma(t)f_N \quad (7)$$

where $\alpha(t)$, $\beta(t)$, $\gamma(t)$ are time varying scaling coefficients, the discrimination operation corresponding results can be computed using the normalized projection of the vector set:

$$\alpha = \frac{u_N \cdot n_{FH}}{a_N \cdot n_{FH}} \quad \beta = \frac{u_N \cdot n_{AF}}{h_N \cdot n_{AF}} \quad \gamma = \frac{u_N \cdot n_{HA}}{f_N \cdot n_{HA}} \quad (8)$$

If all three of the vapors are present in the test measurements, and there are no vapors detected other than from the selected un-mixed vapor group, there may be instances $t_0$ when $\alpha(t_0) + \beta(t_0) + \gamma(t_0) = 1$. This depends on the vapor reservoir and evaporation properties. However, if the above sum of the scaling coefficients is greater than unity, then the discrimination operation indicates that the projections of the vapor vector under test are outside the configuration volume defined by Eq. 4, and therefore are not a match to some of the members of the group $a_N$, $f_N$, and $h_N$. In the case that any one of the above coefficients $\alpha$, $\beta$, $\gamma$, is greater than 1, and the overall sum is between 0 and 1, there must be at least another one which will be negative in value, and therefore both are non-matches for the given group.

In general the operational vector construct outlined above will not yield absolute zero results in operations like that of Eq. 6. The detection system and the choice of the spectrally filtered vapor vector set will include some experimental uncertainty. This uncertainty will produce matching or mismatching errors. Optimizing the functional form of $F_1(k, k_1, \delta k_1)$, meaning: the filter/window extent $\delta k_1$, the position of the filter/window ($k_1$) in the spectral range of interest ($\Delta k$), and the relative position of the filters with respect to each other, will result in well-defined un-mixed vapor vectors, and this in turn will make the discrimination operations more precise.

The ability of the CDSD method to differentiate the presence of any one vapor from a select group was tested as well. To include the effects of the discriminating coefficients sum-result in the computed individual discriminating coefficient values, we chose to display a sum-weighted value for each coefficient, i.e., normalizing the coefficients to their sum:

$$\underline{\alpha} = \frac{\alpha}{\alpha + \beta + \gamma}; \quad \underline{\beta} = \frac{\alpha}{\alpha + \beta + \gamma}; \quad \underline{\gamma} = \frac{\alpha}{\alpha + \beta + \gamma} \quad (9)$$

where $\alpha$, $\beta$, $\gamma$ are the normalized coefficients of acetone, hexanes, and fuel oil, respectively.

This ratio guarantees that the computed results will be a fraction of the total operation calculation, and that large sum values will suppress individual coefficients, thus indicating no matches with the selected un-mixed vapor.

Figure 7:
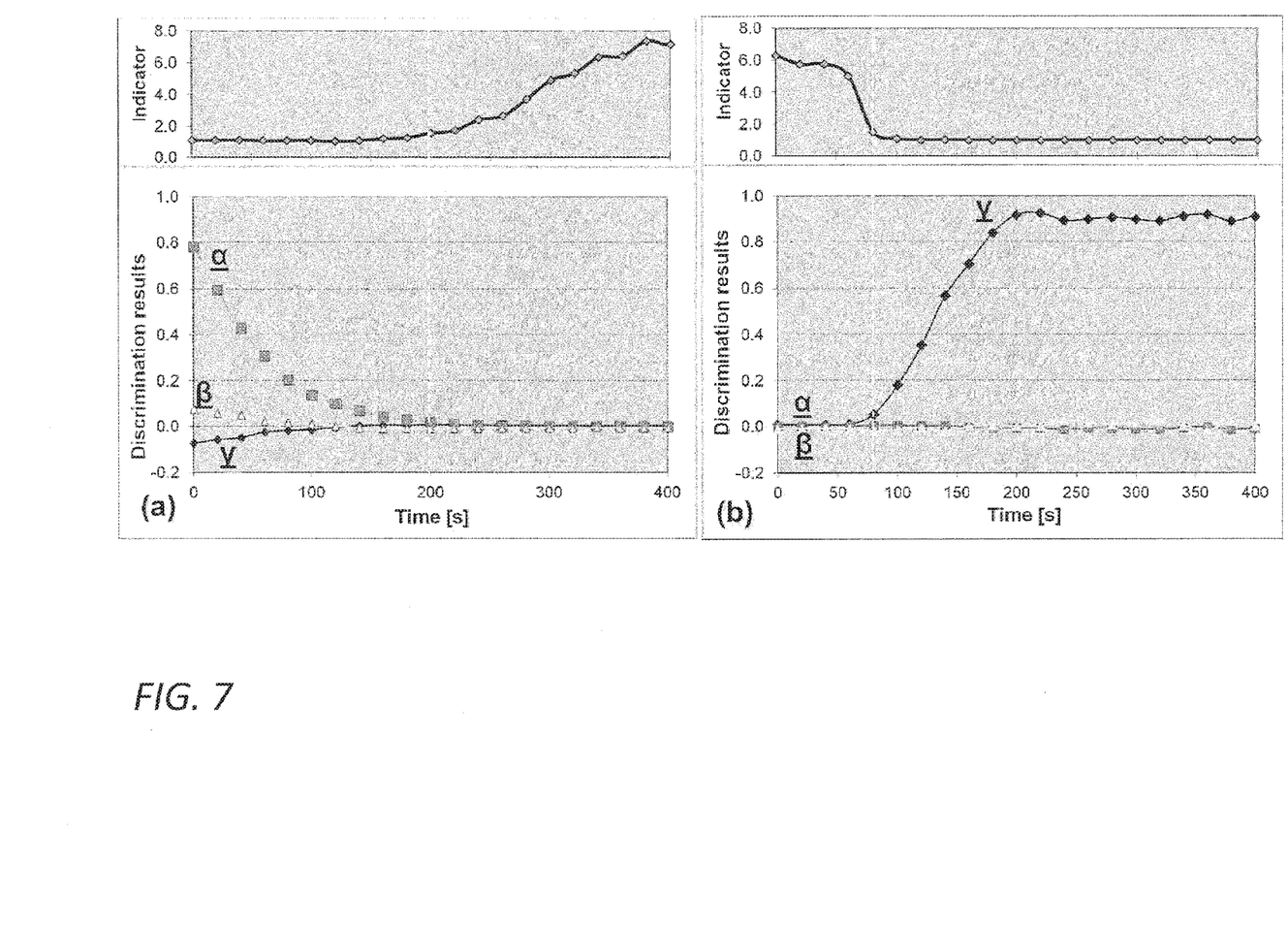

In one trial, we used acetone alone and in the other fuel oil alone. The system was thoroughly purged between runs, flowing dry nitrogen through it for a number of hours. The results of the matching indicator ($\alpha + \beta + \gamma$) and of each weighted discriminating coefficients (Eq. 9) in the test are shown in FIG. 7. For the first 180 s (10 absorption spectra) of the experiment, CDSD 10 identified one of the as-received chemical vapors present, and from 200 s and beyond it indicated no matches to any of the vapors from the original set. In the fuel oil trial, the indicator was present from 80 s and beyond, whereas no vapor was present earlier. The coefficients did not vary significantly after 360 s, indicating that the vapors flowing through the system had reached a steady state. The individual discriminating coefficients are plotted as fractions to their overall sum for each instance. This allows for clear comparisons between the operations at each instance and through the entire measurement interval. For the acetone trial displayed in FIG. 8a, the corresponding coefficient ($\alpha$) shows initially a high fractional value, which decays with time to zero. The other two coefficients have in all instances values much lower than $\alpha$, with the fuel oil coefficient ($\gamma$) actually taking negative values initially, which further indicates complete absence from this trial. The hexanes coefficient ($\beta$) shows positive values for the first 80 s of the experiment, however, the comparative ratio to acetone is never higher than 1:10. After 200 s the finite initial volume of acetone vapor has moved through the detection system, and the discrimination results $\alpha$, $\beta$, $\gamma$ become zero.

In the case of fuel oil ($\gamma$), shown in FIG. 7b, we observe an initial absence of all detectable vapors, followed by a gradual increase in the detection of fuel oil. This result is reasonable, since the evaporation rate constant for FO is 0.04, whereas the corresponding constant for acetone is 14.4. The data clearly shows that it takes 60 s from the start of the experiment for the FO vapors to reach the detecting cell, and then another 140 s to reach the maximum vapor concentration. For the rest of the data collected the slow evaporation rate is enough to maintain the presence of FO in the cell. The discrimination results show clearly the time evolution of the event, identifying FO and not any of the other vapors in the group.

Mixtures of acetone, hexanes, and FO vapors from solutions containing 50% FO with 50% acetone or hexanes were measured as well. Due to their relative evaporation rate differences, and the observations from the un-mixed vapor trials, the expectation was that, if the discriminating comparison was sensitive to each component from the mixture, the system flow-through dynamics should be noticeable. The trial with the mixture of acetone and FO, clearly identified the time evolution of the test. Acetone is present from the initial observation, with $\alpha$ decaying thereafter, where FO is steadily increasing its presence in the flowing cell, peaking in value at 120 s. In the first 60 s of the time sequence, the hexanes signal ($\beta$) is not zero, and after 140 s it becomes negative. This small value of $\beta$ within the first 80 s of the experiment is attributed to the weak overall signal due to the slow evaporation of the fuel oil. Because the signal is weak, the system decides that this "something" may be hexanes ($\beta$) or fuel oil ($\gamma$) and registers as such. As the experiment progresses, the relative strength of the signal arising from the fuel oil increases (as more fuel oil evaporates and enters the FTIR) and the system begins to clearly identify the second component present as fuel oil. Thus, the value for $\gamma$ increases while the value for $\beta$ decreases (until it reaches zero around t=100 s) indicating that the system has clearly identified fuel oil as being present and hexanes as not present. This can be considered as signal "crosstalk", and is related to the minimum discrimination levels (detectivity) for the signals measured.

Figure 8:
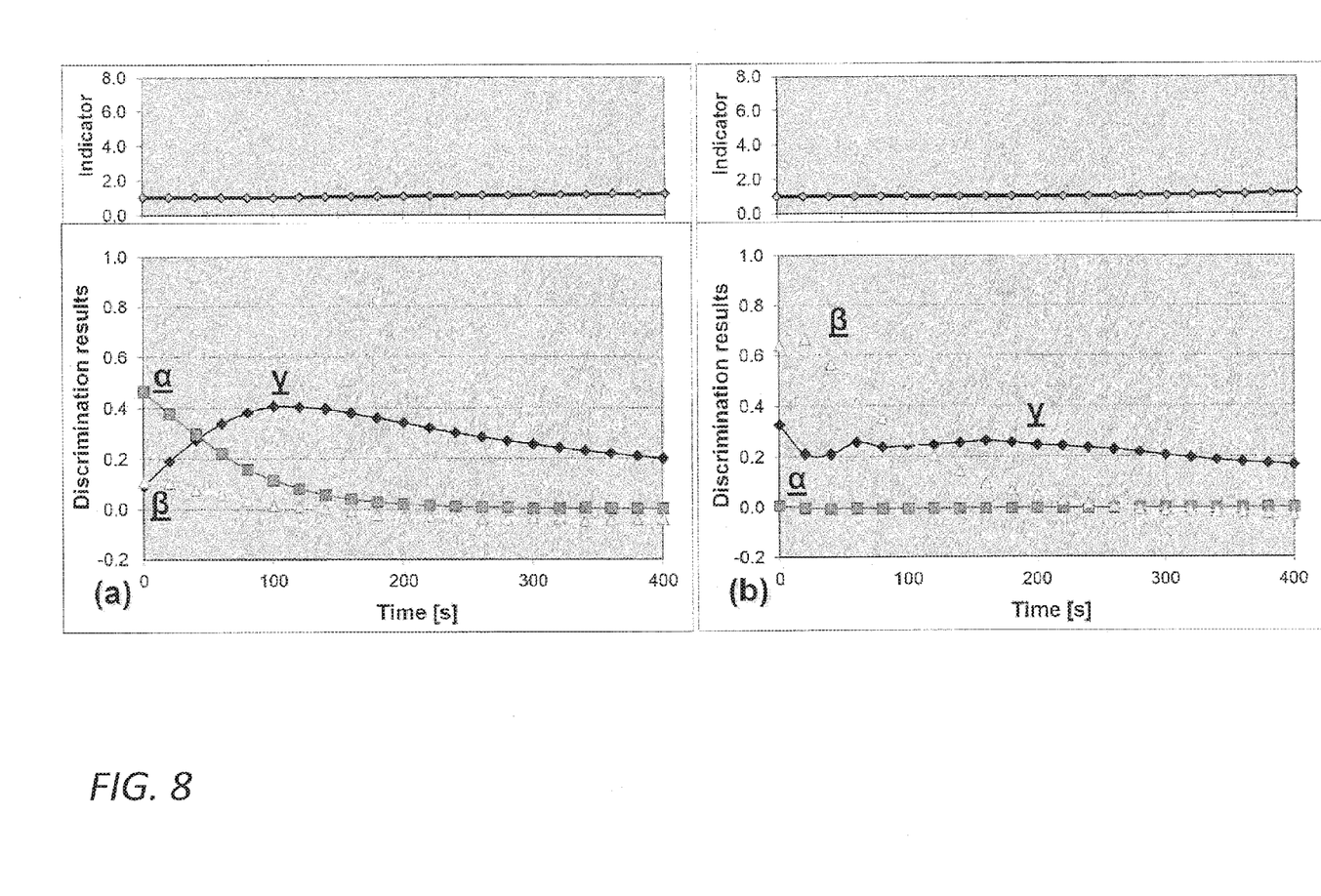

FIG. 8b shows the results from a trial with a mixture of hexanes and FO. The discrimination operation clearly identifies hexanes ($\beta$) initially peaking in signal, and then decaying to zero after 250 s of observation. During the same interval, FO ($\gamma$) is simultaneously detected, and its signal persists to a time longer than 400 s. Acetone ($\alpha$) is clearly absent. This result, when compared to the acetone/FO mixture is also reasonable, since the evaporation rate constant for hexanes is much greater than FO. Further, optimization of the filter windowing functions minimizes the detection uncertainty.

The CDSD method of the present invention has high significance in the field of chemical sensing, as it is capable of determining the presence or absence of particular target vapors, even in the presence of highly similar spectral absorption vapors (interferants), with only a single spectrum, collected in 10-20 seconds. The system used to test out the method consisted of a finite quantity of vapors forced through a gas line, not a static sample cell, and the results clearly identified vapor types at different stages of evaporation and transition. A key aspect is the extension of the configuration space, and the vector operations within it, in contrast to the vector projection methods used by LDA or Kromoscopy. This new approach allows for simpler computations, in a larger configuration space, instead of a determination of the maximum deviation of projections that LDA or Kromoscopy are based on. The results can be obtained quickly, with high accuracy and low uncertainty, in a dynamically changing gaseous environment. Detectivity of chemical vapors are possible with target presence lower than 1 part-per-million (ppm). The operations are limited to finite matrix multiplications, which simplifies the demands for computational power on small, handheld, and portable systems for chemical sensing applications.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A comparative discrimination spectral detection (CDSD) system for the identification of chemicals with overlapping spectral signatures, comprising:
    a radiation source configured for delivering radiation to a sample;
    a radiation collector configured for collecting radiation from the sample;
    a plurality of beam splitters configured for splitting the radiation collected from the sample into a plurality of radiation beams;
    a plurality of optical filters configured for filtering the plurality of radiation beams;
    a plurality of radiation detectors configured for detecting the plurality filtered radiation beams; and
    a processor configured for:
        receiving a set of reference spectra related to a set of target chemicals and generating a set of base vectors for the set of target chemicals from the set of reference spectra, wherein the set of base vectors define a geometrical shape in a configuration space;
        receiving a set of filtered test spectra from the plurality of radiation detectors and generating a set of test vectors in the configuration space from the set of filtered test spectra;
        assessing a geometrical relationship of the set of test vectors and the geometrical shape defined by the set of base vectors in the configuration space; and
        based on the assessed geometrical relationship of the set of test vectors and the geometrical shape defined by the set of base vectors in the configuration space, establishing a probability that a given test spectrum of the set of filtered test spectra matches a given reference spectrum of the set of reference spectra;
        wherein the set of base vectors define a polygon having a volume in the configuration space.

2. The CDSD system of claim 1, wherein the radiation source comprises an infrared (IR) illuminator that emits radiation in one or more of the near-infrared (NIR), the mid-wave infrared (MWIR), and the long-wave infrared (LWIR).

3. The CDSD system of claim 1, wherein the radiation collector comprises an infrared (IR)-compatible optical system of lenses and windows.

4. The CDSD system of claim 1, wherein the plurality of beam splitters each comprise one or more optical plates with predetermined optical reflections and transmissions.

5. The CDSD system of claim 1, wherein the plurality of optical filters each comprise a glass filter with a wavelength pass-band peaked at or adjacent to a wavelength of interest.

6. The CDSD system of claim 1, wherein the plurality of radiation detectors each comprise one of a thermal detector and a photon detector.

7. The CDSD system of claim 1, wherein, if the given test spectrum matches a given reference spectrum, then a given test vector will fall at least partially within the volume of the polygon in the configuration space and have predetermined relationships with the sides and surface normals of the polygon.

8. The CDSD system of claim 1, wherein, if the given test spectrum does not match a given reference spectrum, then a given test vector will fall at least partially outside of the volume of the polygon in the configuration space and not have predetermined relationships with the sides and surface normals of the polygon.

9. A comparative discrimination spectral detection (CDSD) method for the identification of chemicals with overlapping spectral signatures, comprising:
   delivering radiation to a sample using a radiation source;
   collecting radiation from the sample using a radiation collector;
   splitting the radiation collected from the sample into a plurality of radiation beams using a plurality of beam splitters;
   filtering the plurality of radiation beams using a plurality of optical filters;
   detecting the plurality filtered radiation beams using a plurality of radiation detectors; and
   providing a processor configured for:
      receiving a set of reference spectra related to a set of target chemicals and generating a set of base vectors for the set of target chemicals from the set of reference spectra, wherein the set of base vectors define a geometrical shape in a configuration space;
      receiving a set of filtered test spectra from the plurality of radiation detectors and generating a set of test vectors in the configuration space from the set of filtered test spectra;
      assessing a geometrical relationship of the set of test vectors and the geometrical shape defined by the set of base vectors in the configuration space; and
      based on the assessed geometrical relationship of the set of test vectors and the geometrical shape defined by the set of base vectors in the configuration space, establishing a probability that a given test spectrum of the set of filtered test spectra matches a given reference spectrum of the set of reference spectra;
   wherein the set of base vectors define a polygon having a volume in the configuration space.

10. The CDSD method of claim 9, wherein the radiation source comprises an infrared (IR) illuminator that emits radiation in one or more of the near-infrared (NIR), the mid-wave infrared (MWIR), and the long-wave infrared (LWIR).

11. The CDSD method of claim 9, wherein the radiation collector comprises an infrared (IR)-compatible optical system of lenses and windows.

12. The CDSD method of claim 9, wherein the plurality of beam splitters each comprise one or more optical plates with predetermined optical reflections and transmissions.

13. The CDSD method of claim 9, wherein the plurality of optical filters each comprise a glass filter with a wavelength pass-band peaked at or adjacent to a wavelength of interest.

14. The CDSD method of claim 9, wherein the plurality of radiation detectors each comprise one of a thermal detector and a photon detector.

15. The CDSD method of claim 9, wherein, if the given test spectrum matches a given reference spectrum, then a given test vector will fall at least partially within the volume of the polygon in the configuration space and have predetermined relationships with the sides and surface normals of the polygon.

16. The CDSD method of claim 9, wherein, if the given test spectrum does not match a given reference spectrum, then a given test vector will fall at least partially outside of the volume of the polygon in the configuration space and not have predetermined relationships with the sides and surface normals of the polygon.

* * * * *